(12) United States Patent
Feron et al.

(10) Patent No.: US 10,640,626 B2
(45) Date of Patent: May 5, 2020

(54) COMPOSITIONS OF MIXED DIESTERS OF 1,4: 3,6-DIANHYDROHEXITOL

(71) Applicant: ROQUETTE FRERES, Lestrem (FR)

(72) Inventors: Thierry Feron, Fouquieres les Bethune (FR); Arnaud Verraes, Wavrin (FR); Herve Wyart, Cuinchy (FR); Catherine Baurain, Locon (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 14/647,226

(22) PCT Filed: Nov. 26, 2013

(86) PCT No.: PCT/FR2013/052865
§ 371 (c)(1),
(2) Date: May 26, 2015

(87) PCT Pub. No.: WO2014/080151
PCT Pub. Date: May 30, 2014

(65) Prior Publication Data
US 2015/0322238 A1    Nov. 12, 2015

(30) Foreign Application Priority Data
Nov. 26, 2012   (FR) ..................... 12 61253

(51) Int. Cl.
*C08K 5/1535* (2006.01)
*C07D 493/04* (2006.01)
*C08J 3/18* (2006.01)

(52) U.S. Cl.
CPC .......... *C08K 5/1535* (2013.01); *C07D 493/04* (2013.01); *C08J 3/18* (2013.01); *C08J 2327/06* (2013.01)

(58) Field of Classification Search
CPC ............................ C07D 493/04; C08K 5/1535
See application file for complete search history.

(56) References Cited

U.S. PATENT DOCUMENTS

| | | | | |
|---|---|---|---|---|
| 2,387,842 A * | 10/1945 | Soltzberg | ............. | C07D 493/04 549/464 |
| 6,693,209 B2 * | 2/2004 | Van Es | ................ | C07D 493/04 549/483 |
| 8,129,549 B2 * | 3/2012 | Fuertes | ................ | C07D 493/04 549/464 |
| 9,493,632 B2 * | 11/2016 | Grass | ................... | C07D 493/04 |
| 9,505,909 B2 * | 11/2016 | Grass | ................... | C07D 493/04 |
| 2009/0301348 A1 | 12/2009 | Grass et al. | | |
| 2012/0116101 A1 | 5/2012 | Fuertes et al. | | |
| 2014/0088233 A1 * | 3/2014 | Kann | ...................... | C08L 27/06 524/296 |
| 2014/0322151 A1 * | 10/2014 | Fricke | .................. | A61K 8/4973 424/67 |
| 2014/0336092 A1 * | 11/2014 | Chen | .................... | C10M 129/72 508/308 |

FOREIGN PATENT DOCUMENTS

| | | | | |
|---|---|---|---|---|
| DE | 102011119033 A1 * | 9/2012 | .......... | A61K 8/4973 |
| WO | 99/32427 | 7/1999 | | |
| WO | 99/45060 | 9/1999 | | |
| WO | 00/78853 | 12/2000 | | |
| WO | 2006/103338 | 10/2006 | | |
| WO | 2008/095571 | 8/2008 | | |
| WO | 2013/092649 | 6/2013 | | |
| WO | 2013/092655 | 6/2013 | | |
| WO | WO 2013092649 A1 * | 6/2013 | .......... | C07D 493/04 |

OTHER PUBLICATIONS

C-810, P&G Chemicals, 2015, 1 page.*
International Search Report dated Jan. 23, 2014, corresponding to PCT/FR2013/052865.
Hachihama, et al; "Preparation of Plasticizers from Carbohydrate Sources. I. Levulinic Acid Esters. II Sorbide Esters"; vol. 3, No. 72; Jan. 1, 1953.

* cited by examiner

*Primary Examiner* — Brieann R Johnston
(74) *Attorney, Agent, or Firm* — Oliff PLC

(57) ABSTRACT

A method for producing a composition of diesters, includes a step including the esterification of 1,4:3,6-dianhydrohexitol by a composition of carboxylic acids, the composition including: at least an acid having formula C7H15COOH (X) and an acid having formula C9H19COOH (Y), the mass ratio (X)/(Y) varying between 10/90 and 90/10.

7 Claims, No Drawings

COMPOSITIONS OF MIXED DIESTERS OF 1,4:3,6-DIANHYDROHEXITOL

FIELD OF THE INVENTION

The invention relates to a composition that is liquid at room temperature, comprising mixtures of 1,4:3,6-dianhydrohexitol esters. A second subject of the invention relates to a process for manufacturing said composition. Another aspect of the invention relates to the use of this composition for plasticizing polymers.

PRIOR ART

Due to their numerous advantages, the use of synthetic polymers has become generalized in numerous applications since the turn of the century.

However, these polymers may have drawbacks, such as, in particular, their mechanical properties, which may be insufficient for certain uses. For example, they may have a very low elongation at break at room temperature or poor impact strength.

Furthermore, it may be necessary to modify the meltphase behavior of these polymers, especially in order to be able to use them in transformation processes such as coating or calendering. In other words, it is necessary for the polymer to have passed its melting point, or its gel temperature, and thus for the polymer to have, in this gelled state, a viscosity that is suited to the forming process in order to be able to be correctly transformed.

To be able to use them in wider applications, it is also necessary to modify the properties of these polymers, for example to make them more flexible or more resistant to impacts, or alternatively to allow them to have a softer appearance.

To do this, these polymers may be mixed with "plasticizers".

The term "plasticizer" means any product which, when mixed in sufficient amount with a polymer, has the function of reducing the glass transition temperature of said polymer.

By reducing the glass transition temperature of the polymer, its flexibility is increased and the mechanical properties of this plasticized polymer are modified. Thus, by adding a plasticizer to a polymer composition, a reduction in the modulus, especially in the modulus at 100% elongation, a reduction in the breaking strength and/or an increase in the deformation at break are generally observed.

These modified properties of the polymer then allow it to be used in more varied applications, for example in films or flexible sheets.

During the plastic implementation process, plasticizers are generally mixed with the polymer, which allows a decrease in the softening point of the polymer.

This mixing may take place via various implementation processes.

In the case of polyvinyl chlorides (PVC), for example, the polymer may be transformed into an object via various techniques for transforming thermoplastic materials, and in particular by extrusion, by calendering or by coating via a process of plastisol type.

In order to obtain this thermoplastic mixture, PVC is mixed with the plasticizer while supplying energy to this system, in the form of temperature and mechanical energy. In the case of extrusion, this mixing takes place in a closed system. In the case of mixing on rolls, this mixing takes place in an open system. The polymer may then be formed, for example via thermoforming or calendering processes.

Generally, a step of dry blending is performed before the thermomechanical mixing step.

According to the plastisol process, a mixture is generally prepared to form a PVC paste, this paste is then formed via a coating or molding step, and the paste is then heated in an oven to form the component.

Irrespective of the process, the polymer needs to be correctly melted or gelled in order to be able to form satisfactorily the object obtained at the end of the process.

For reasons of ease of storage, use and metering of the plasticizer, plasticizers that are liquid at room temperature are generally used.

For all these processes for obtaining thermoplastic mixtures from PVC, plasticizers of the phthalic ester family are very often still used. They are, at the present time still, very generally dioctyl phthalate or diisononyl phthalate. These plasticizers are very effective for plasticizing polymers, and are readily available on the market, for a relatively low cost.

However, due to the toxicity problems of phthalates, other plasticizers have also been developed in recent years, such as cyclohexanepolycarboxylic acid and derivatives thereof, which have been the subject of patent applications WO 00/78853 and WO 99/32427. By way of example, mention may be made of the diisononyl ester of 1,2-cyclohexanedicarboxylic acid (DINCH) sold by BASF under the brand name Hexamoll®.

Other plasticizers that may also be mentioned include glycerol ester derivatives, such as Grindsted® Soft-N-Safe obtained from glycerol and castor oil and sold by the company Danisco. These plasticizers have the advantage of being obtained from biosourced products.

The use of 1,4:3,6-dianhydrohexitol derivatives as polymer plasticizers has already been described in document WO 99/45060. These derivatives do not have the toxicity problems of phthalates. These plasticizers also have the advantage of being partially biosourced, or even totally biosourced. Said patent application describes, in the examples, the following plasticizers that are liquid at room temperature: isosorbide dioctanoate, isosorbide dibutanoate, isosorbide dihexanoate and isosorbide bis(2-ethylhexanoate). These plasticizers are also described in document WO 2008/095571 A1, which describes aliphatic diesters containing 9 carbon atoms. The document *Preparation of plasticizers from carbohydrate sources. I. Levulinic acid esters. II. Sorbide esters*, (Hachihama et al., Technology reports of the Osaka University, Vol. 3, No. 72, 1953, pages 191-200) describes aliphatic esters containing 8 carbon atoms and also aliphatic esters containing 10 carbon atoms. U.S. Pat. No. 2,387,842 A describes mixed aliphatic diesters, these also being useful as plasticizers.

The mechanical properties of polymers plasticized with these derivatives are excellent, close to those obtained with plasticizers of phthalate type.

In the context of its research, the Applicant Company has, however, found that these compounds, and in particular isosorbide dioctanoate, have a tendency to "migrate" out of the object formed from the plastic. It may also be observed, for example, that the plasticizer "exudes". Now, migration of the plasticizer may have, as consequences, a loss over time of mechanical and/or optical properties of the polymer, degradation of the appearance and of the feel, or may even pose printing defect problems when it is desired to print the surface of the polymer in a second stage. For certain applications, the resistance to leaching, i.e. migration in a bath of hot water, may also be a decisive property, especially, for example, for the manufacture of geomembranes. Moreover, some of these compounds have another problem:

they may have a volatility that is still a little high. This may be an inconvenience, in particular at the time when the transformer mixes the plasticizer with the polymer, and all the more so when he uses an open mixing system. Specifically, there is a slight loss of plasticizer during the transformation.

There thus remains a need to find novel plasticizing compositions, which are liquid at room temperature, these compositions making it possible to solve the problems mentioned previously and in particular to limit the migration observed in polymers plasticized with said compositions.

SUMMARY OF THE INVENTION

The Applicant has precisely, to its merit, managed to find a particular composition of dianhydrohexitol diesters for plasticizing polymers very efficiently, while at the same time limiting the migration problems described previously.

This 1,4:3,6-dianhydrohexitol diester composition may be obtained via a manufacturing process, which is the subject of the present invention, said process comprising a step of esterifying 1,4:3,6-dianhydrohexitol with a carboxylic acid composition, said carboxylic acid composition comprising at least one acid of formula $C_7H_{15}COOH$ (X) and one acid of formula $C_9H_{19}COOH$ (Y), the mass ratio (X)/(Y) ranging from 10/90 to 90/10.

In contrast with 1,4:3,6-dianhydrohexitol decanoates, for example, this composition also has the advantage of being liquid at room temperature, which allows easy metering of the plasticizer during the manufacture of polymeric objects plasticized with this composition.

The composition also has the advantage of being able to be manufactured from a carboxylic acid composition that is less expensive than those used for the manufacture of certain 1,4:3,6-dianhydrohexitol diesters already known from patent application WO 99/45060, especially 1,4:3,6-dianhydrohexitol dioctanoates which are manufactured exclusively from n-octanoic acid as carboxylic acid.

DETAILED DESCRIPTION OF THE INVENTION

The process according to the invention comprises a step of esterifying 1,4:3,6-dianhydrohexitol with a carboxylic acid composition.

Before performing the actual esterification step, the process according to the invention generally comprises a step of introducing 1,4:3,6-dianhydrohexitol and a step of introducing carboxylic acids or a carboxylic acid composition into a reactor.

The 1,4:3,6-dianhydrohexitol used in the process according to the invention may be chosen from isomannide, isoidide and isosorbide, or mixtures thereof, preferentially isosorbide. The diesters thus manufactured via the process according to the invention are then, respectively, isomannide, isoidide or isosorbide diesters or mixtures of these diesters.

The carboxylic acid composition that is useful in the process according to the invention comprises at least two carboxylic acids of formula $C_7H_{15}COOH$ (X) and of formula $C_9H_{19}COOH$ (Y) and optionally one or more carboxylic acids other than (X) and (Y).

The two acids X and Y may be, dependently or independently of each other, linear or branched, and are preferentially linear.

These optional carboxylic acids, other than the acids (X) and (Y), which may be used in the carboxylic acid composition may be saturated or unsaturated, preferably saturated, monocarboxylic acids. These carboxylic acids may comprise from 2 to 36 carbon atoms, provided that they do not correspond to formula (X) or to formula (Y). These carboxylic acids may be acids comprising 6, 12 or 14 or 18 carbon atoms, especially 12 carbon atoms. They are, for example, hexanoic acid, lauric acid, myristic acid, oleic acid or linoleic acid, preferentially lauric acid.

The carboxylic acid composition used in the process according to the invention may comprise, relative to its total mass, at least 50% by mass of acids (X) and (Y), for example at least 65%, at least 80%, for example at least 90%, and may especially consist of the acids (X) and (Y).

Advantageously, the mass ratio (X)/(Y) ranges from 15/85 to 75/25.

Preferably, the mass ratio (X)/(Y) ranges from 20/80 to 65/35.

When the mass ratio (X)/(Y) does not exceed 65/35, the composition that may be obtained via the process of the invention also has the advantage of being markedly less volatile.

Most preferentially, the mass ratio (X)/(Y) ranges from 25/75 to 55/45.

According to this particularly preferred variant of the process according to the invention, the composition that may be obtained makes it possible, when it is used for plasticizing polymers, to obtain very low migration. It also has the advantage of being inexpensive.

According to a most preferred variant, the mass ratio (X)/(Y) ranges from 25/75 to 45/55 and most preferentially from 26/74 to 34/66. It is in these most preferred ranges that a composition which has the most improved properties described above is obtained.

According to one embodiment, the mole ratio (X)/(Y) is other than 25/75, and/or 40/60, and/or 45/55, and/or 50/50, and/or 57/43, and/or 58/42, and/or 65/35, and/or 75/25 and/or 80/20 and/or 85/15.

According to one embodiment, the mole ratio (X)/(Y) is not included in the following ranges: 45/55 to 85/15, 45/55 to 75/25, 45/55 to 65/35 or 50/50 to 65/35.

The esterification step of the process according to the invention may be performed via any known method for esterifying 1,4:3,6-dianhydrohexitol with a carboxylic acid, said process differing from the processes of the prior art in that use is made, instead of the carboxylic acid conventionally used, of a carboxylic acid composition comprising at least one acid (X) and one acid (Y), the mass ratio (X)/(Y) ranging from 10/90 to 90/10.

By varying the mass ratio of the fatty acids, the amounts of diesters formed in this step are varied as described hereinbelow.

The esterification reaction may be performed under the standard implementation conditions already used in the literature. These esterification methods are described, for example, in documents WO 99/45060 A1 or WO 2006/103 338 A1.

To form the diester composition, 2 mol of carboxylic acid are generally reacted per mole of 1,4:3,6-dianhydrohexitol in the esterification reactor.

The total sum of moles of carboxylic acids (X), (Y) and of other optional carboxylic acids introduced into the reactor advantageously ranges from 2 to 20 per 1 mol of 1,4:3,6-dianhydrohexitol, preferably from 2.5 to 5 and most preferentially from 2.8 to 3.5.

The esterification step may be performed in the presence of at least one acid catalyst. The acid catalyst used for the esterification may be of very varied nature, and, for example, may be an acid chosen from hypophosphorous acid, hydrochloric acid, sulfuric acid, para-toluenesulfonic acid (PTSA), methanesulfonic acid (MSA), trifluoromethanesulfonic acid, trifluoroacetic acid, trichloroacetic acid, tin 2-ethylhexanoate, phosphotungstic acid and silicotungstic acid or a mixture of these acids or a macroporous or non-macroporous resin comprising at least one of these acids. Preferably, the catalyst comprises hypophosphorous acid.

In the case of mixtures of catalysts, they may be introduced into the reaction medium simultaneously or separately.

The mass amount of acid catalyst may range from 0.05% to 20%, for example from 0.1% to 10%, relative to the mass of 1,4:3,6-dianhydrohexitol introduced into the reactor.

The temperature in the reactor may range from 90 to 200° C., generally from 100 to 160° C. To perform the esterification reaction, the water is generally removed so as to allow the formation of the diester, this removal possibly taking place, for example, by distillation of the reaction medium. In order to facilitate this removal, the reaction medium may be placed under vacuum, for example to a level ranging from 10 to 200 mbar. The reaction conditions such as the level of vacuum and the temperature during the reaction may be varied.

The esterification reaction generally lasts the time to obtain a satisfactory conversion into 1,4:3,6-dianhydrohexitol diester. It may vary widely and may range from 1 to 10 hours.

A step of neutralizing the catalyst introduced may also be performed, by introducing a base, for example sodium hydroxide, in molar amounts equivalent to the molar amounts of catalyst introduced.

The manufacturing process may also comprise a step of purifying the composition derived from the esterification step. This advantageously consists of at least one evaporation step, for example by distillation, for removing the majority or virtually all of the carboxylic acid still present after the esterification step. During this step, the diester composition may be subjected to temperature conditions of between 100 and 250° C. and to reduced pressures of between 0.1 and 50 mbar. Preferably, this step takes place in a continuous evaporator. Such an evaporator, for example of "falling film" type or, better still, of scraped film or "short path" type, makes it possible to limit the temperatures and residence times to which the composition is subjected after the esterification step.

The process may also comprise a step of decolorizing the diester composition, for example by using active charcoals or hydrogen peroxide. The treatment with active charcoal takes place, for example, by placing the composition in contact with 1% to 3% by weight of active charcoal. The temperature during this treatment may be in the region of 100° C. The time is generally a few tens of minutes, for example about one hour. At the end of the treatment, the active charcoal is separated out by filtration. A standard decolorizing treatment with hydrogen peroxide consists, for example, in introducing into the composition to be decolorized, over a period ranging, for example, from 30 to 60 minutes, from 0.5% to 2% of 100% hydrogen peroxide, at a temperature of between 90° C. and 100° C., and the composition is then stirred for one to two hours at this temperature. When it is desired to combine these two types of decolorizing treatment, the hydrogen peroxide treatment preferably precedes that with active charcoal. The reason for this is that the active charcoal makes it possible to destroy the peroxides that may be present.

As explained previously, another subject of the invention relates to a 1,4:3,6-dianhydrohexitol diester composition that may be obtained via the manufacturing process described previously.

This diester composition which may be obtained from a carboxylic acid composition comprising, in addition to the acids (X) and (Y), one or even more other carboxylic acids, cannot be defined more satisfactorily than by its manufacturing process.

Specifically, when this carboxylic acid composition comprises one or more carboxylic acids other than the acids (X) and (Y), very complex and diverse compositions are obtained, which will depend on the nature and amount of the carboxylic acids other than the acids (X) and (Y) used.

However, the compositions according to the invention may be defined more readily when the mixture of (X) and (Y) is used exclusively as carboxylic acid composition.

By way of example, when the process according to the invention is performed using a carboxylic acid composition consisting of (X) and (Y) in which the mass ratio (X)/(Y) is equal to 70/30, the composition produced comprises, by mass:

about 48% of diester (A) of formula:

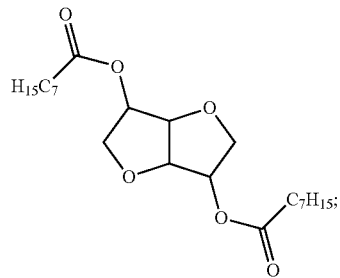

about 43% of diester (B) of formula:

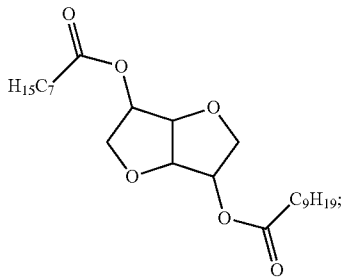

about 9% of diester (C) of formula:

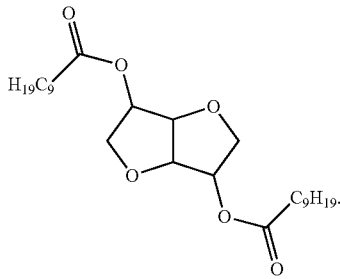

A person skilled in the art can thus manufacture the compositions according to the invention and also the preferred variants thereof by using the process described previously and by varying the mass ratio (X)/(Y). Other examples of diester compositions that may be produced according to the process of the invention are also featured in the examples of the present patent application.

Thus, a subject of the invention is also a composition that may be obtained using the process described previously, said composition comprising:
from 0.5% to 82% by mass of diester (A);
from 15% to 55% by mass of diester (B);
from 0.5% to 82% by mass of diester (C);
the amounts being given relative to the total mass of the diesters (A), (B) and (C).

The mass amounts of different diesters may be determined by gas chromatography. It is possible, for example, to refer to the detailed analytical method featured in the examples.

This composition is most particularly preferred since it is this one which makes it possible, when it is used for plasticizing polymers, to obtain the lowest migration. It also has the advantage of being inexpensive.

Preferably, the composition is such that:
diester (A) has the following formula:

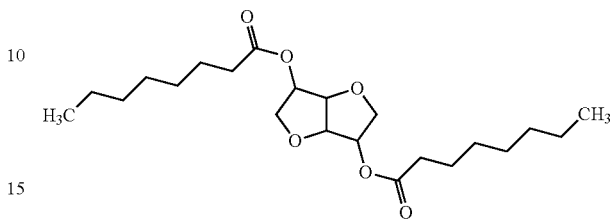

diester (B) has the following formula:

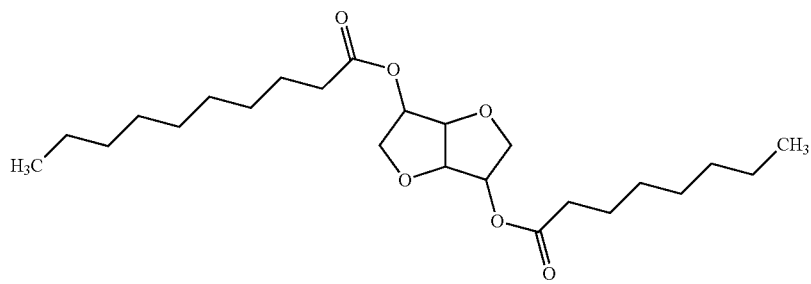 [SMILES: CCCCCCCCCC(=O)OC1COC2C(OC(=O)CCCCCCC)COC12]

diester (C) has the following formula:

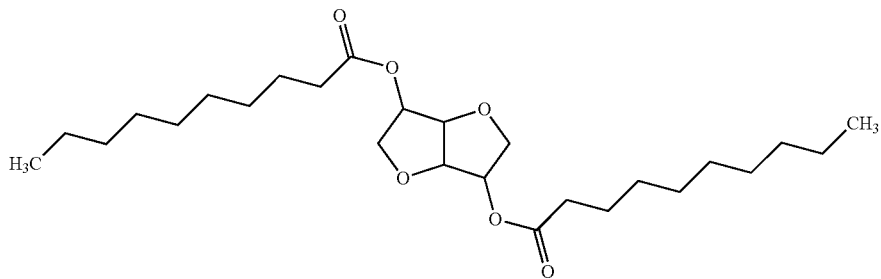 [SMILES: CCCCCCCCCC(=O)OC1COC2C(OC(=O)CCCCCCCCC)COC12]

Advantageously, the composition comprises:
from 1% to 57% by mass of diester (A);
from 25% to 54% by mass of diester (B);
from 5% to 73% by mass of diester (C);
the amounts being given relative to the total mass of the diesters (A), (B) and (C).

Preferentially, the composition comprises:
from 3% to 43% by mass of diester (A);
from 31% to 53% by mass of diester (B);
from 11% to 65% by mass of diester (C);
the amounts being given relative to the total mass of the diesters (A), (B) and (C). This preferred composition also has the advantage of being markedly less volatile.

Most preferentially, the composition comprises:
from 5% to 31% by mass of diester (A);
from 37% to 52% by mass of diester (B);
from 19% to 57% by mass of diester (C);
the amounts being given relative to the total mass of the diesters (A), (B) and (C).

The composition that may be obtained via the process according to the invention already described generally comprises the following residual species, occasionally in trace amount: 1,4:3,6-dianhydrohexitol monoesters, residual acids, or even water.

The composition according to the invention may thus have, relative to its total mass, at least 80% by mass of diester, for example at least 90%, preferentially at least 95%, most preferentially at least 98%.

Preferentially, the diesters (A), (B) and (C) constitute at least 50% of the mass of the 1,4:3,6-dianhydrohexitol diesters, preferentially at least 80%, most preferentially at least 90%, for example they constitute all of the 1,4:3,6-dianhydrohexitol diesters.

Preferably, at least one of the diesters of the composition is an isosorbide diester. Preferably, the diester composition is an isosorbide diester composition.

According to one variant of the composition according to the invention, it contains at least 90% carbon derived from renewable material according to standard ASTM D6866.

As 1,4:3,6-dianhydrohexitol may be obtained from mannitol, iditol and sorbitol, which are themselves obtained from starch, the 1,4:3,6-dianhydrohexitol esters that are useful in the invention also have the advantage of being able to be partially biosourced, or even totally biosourced, if carboxylic acid compositions that are also totally biosourced are used.

As described previously, the composition according to the invention, which has the advantage of being liquid at room temperature (25° C.), is particularly useful for plasticizing polymers.

The Applicant has found that the plasticizing composition made it possible to plasticize polymers excellently, at least as satisfactorily as with 1,4:3,6-dianhydrohexitol dioctanoates. Furthermore, still relative to polymers plasticized with these dioctanoates, the phenomenon of migration of the plasticizing composition from the polymer is drastically reduced.

The polymer may be chosen from vinyl polymers such as polyvinyl chloride and vinyl chloride copolymers, polyurethanes, polyesters, cellulose-based polymers, starches, acrylic polymers, polyacetates, natural or synthetic rubbers, especially rubbers manufactured from styrene and/or from butadiene such as rubbers of the type such as SBR, BR or NBR, polyamides, and mixtures of these polymers, preferentially polyvinyl chloride. According to the present invention, the term "polyvinyl chloride" means vinyl chloride homopolymers or copolymers comprising vinyl chloride, for example vinyl acetate/vinyl chloride copolymers.

The polymer thus obtained is a polymer plasticized with the composition according to the invention. To a person skilled in the art, this means that the polymer and the plasticizing composition are intimately mixed. The constituents of the plasticizing composition are introduced between the chains of the solid polymer and this results in, after transformation, a plasticized polymer consisting of a solid phase.

Prior to its mixing with the plasticizing composition, the polymer may be in any form, for example in the form of granules or powder.

A polymer paste comprising a mixture of a polymer powder and of the composition according to the invention may also be manufactured. This paste is generally known as a plastisol and makes it possible to form objects via the processes described below. Preferentially, the mean particle diameter of the powder is between 1 and 30 µm, for example between 1 and 20 µm. In the case of polyvinyl chloride, powders of this type may be obtained by preparing PVC by emulsion or microsuspension. This paste is generally obtained by mechanical mixing, preferentially without heating, of the polymer powder with the plasticizing composition.

The mixtures thus obtained are known as plastisols, which are, depending on the amounts of polymer and of plasticizing composition, more or less fluid. Conventionally, plastisols are prepared in rapid mixers of turbomixer type, planetary mixers or slow mixers which are planetary mixers with horizontal Z-shaped paddles.

The plasticizing composition and the polymer are advantageously mixed in mass proportions such that the amount of plasticizing composition ranges from 1 to 900 parts per 100 parts of polymer, advantageously from 5 to 180 parts, and preferentially from 15 to 120 parts of plasticizing composition. They may be introduced into the mixing system via any suitable means, such as a feed hopper, or manually.

In the case of the polymer paste, it is preferred for the amounts of plasticizing composition to range from 30 to 120 parts per 100 parts of polymer powder.

In the plasticized polymer composition, use may also be made, in addition to the plasticizing composition and the polymer, of optional additives. These additives may be chosen from stabilizers, anti-UV agents, fillers, dyes, pigments, swelling agents, emulsifiers, viscosity reducers other than the plasticizing composition, thickeners, mold-release agents, mattifying agents, adhesion agents, antistatic agents, fungicides and odoriferous agents. The amounts of each additive are chosen so as to give the desired properties during the implementation of the process or for the object finally obtained. These additives may be introduced into the composition directly or in the form of a masterbatch. The amount of optional additive generally ranges from 1 to 600 parts per 100 parts of polymer (C), generally from 2 to 80 parts.

According to a first variant of the process for manufacturing the plasticized polymer, the process comprises a step of thermomechanical mixing.

According to this first variant, the thermomechanical mixing step is performed in a mixing system which is a mixer for thermoplastics. This mixer may be chosen from blenders, Buss mixers, roll mixers and extruders.

The plasticizing composition may be introduced in the form of a masterbatch.

The thermomechanical mixing step is performed at a temperature suited to the transformation temperature of the polymer. By way of example, the temperature of the mixture during the thermomechanical mixing is preferentially between 60 and 200° C. for a PVC.

For thermomechanical mixing, use may be made of a polymer in any type of form, especially in the form of granules or a powder.

According to this first variant, a preliminary step of dry blending of the plasticizing composition with the polymer before the thermomechanical mixing is advantageously performed. This dry blending may be performed in a simple mechanical mixer, which may be heated to a temperature below the melting point or gel point of the polymer.

The object may advantageously be formed by calendering, injection molding, extrusion injection molding, intrusion, dipping in a fluidized bed, electrostatic spraying, molding, rotary molding, extrusion molding, sintering, thermoforming, pressing, extrusion forming, extrusion cladding or extrusion blow molding. Use may also be made of coextrusion techniques to form multilayer objects.

According to a second variant, a process of plastisol type is used to form the object according to the invention with the polymer paste described previously.

In this type of process, the implementation step is generally a step of coating, dipping, padding, spraying, casting, molding, slushing or rotary molding of the polymer paste, which makes it possible to form a preformed object.

The heating step of the process is a step of baking of said preformed object, this step generally taking place after the preforming step (this is the case, for example, for coating). It may occasionally also take place during the step of forming of the preformed object (this is the case, for example, for dipping, slushing or rotary molding). This baking step may take place at a temperature of between 60 and 300° C., for example between 100 and 250° C., generally between 140 and 220° C. It may take place in air or under a controlled atmosphere, for example under an inert atmosphere.

The object forming step is preferentially a step of coating the polymer paste onto a support, this coating being performed before the step of baking of said coated support. The coating step may be performed on a textile support, a surfacing mat, metal, a synthetic polymer or a paper.

The coating may be performed using any coating head, for example using a doctor blade or a roll.

According to a first sub-variant, this coating may be "coating on a support" as described above, or, according to a second sub-variant, "coating without a support". In the latter case, the coated support may be detached after baking and the process also comprises a subsequent step of separation of the support to form a film or sheet of plasticized polymer. Such a support may be made of silicone paper.

The baking step is generally performed in an oven, for example a tunnel oven, on a gelling drum or under an infrared ramp.

An object comprising the plasticized polymer composition may also be formed.

The object comprising the plasticized polymer composition may be any type of object, such as a film, a sheet, a granule, a floor covering, a wall covering, a plastic-coated fabric, especially an artificial leather, for example for shoes, for bags or for furniture, a tarpaulin, a liner, for example for a swimming pool, a sun canopy, a flexible container, an item of clothing, a medical product, a bottle, a seal, a protective coating, a showroom dummy, a toy, for example a ball or a doll, a tube, profiles, especially window profiles, motor vehicle parts such as a dashboard, seat, fuel tank or headrest. These parts may be cellular, foam or sponge parts, i.e. comprising air cells. They may also, on the other hand, be compact parts.

One advantage of the compositions according to the invention is that they make it possible to improve the fogging properties of parts made from polymer plasticized with these compositions, and especially from plasticized PVC, when compared with polymer parts plasticized with already-known 1,4:3,6-dianhydrohexitol diester. This is particularly important for use in motor vehicles or in transportation.

Another advantage of the compositions according to the invention is that they make it possible to improve the leaching properties of parts made from polymer, and especially from PVC, plasticized with these compositions, when compared with parts made from polymer plasticized with already-known 1,4:3,6-dianhydrohexitol diester. This is particularly important when the part is exposed to the exterior.

Obviously, improvements are even greater when these compositions are rich in diester, i.e. when the amount of 1,4:3,6-dianhydrohexitol monoesters and/or of residual acids therein is low since these species are known to migrate more easily.

These parts may be covered with a coat of varnish, which makes it possible to further limit this leaching and/or this migration.

The invention will now be detailed in the implementation examples below. It is pointed out that these examples do not in any way limit the subject of the present invention.

EXAMPLES

Analytical Methods

The mass amount of diester in the composition and the mass proportions of each diester (A), (B) and (C) formed is measured by gas chromatography on a Varian 3400 machine with FID detection and a 1077 split/splitless injector. The column used is a J & W Scientific brand DB1 column 30 meters long, with an inside diameter of 0.32 mm, and a film thickness of 0.25 µm. The temperature conditions are: injector and detector: 300° C.; column: program from 100° C. to 320° C. at a rate of 7° C./min, maintenance for 15 minutes at 320° C. Injection takes place in split mode at 80 ml/min, the column head pressure being 14 psi and the carrier gas used is helium.

The mass amount of diester is given by the ratio of the sum of the areas of the compounds corresponding to the isosorbide diesters to the sum of the areas of all of the compounds whose retention time is between 4 and 40 minutes.

The mass distribution of diester is given by the ratio of the area of the diester (A), (B) or (C) to the sum of the areas of these diesters.

Example 1 (Comparative)

A test in accordance with the prior art (TEST 1) is performed according to the following general operating protocol.

146 g of isosorbide (1 mol) and 423 g of n-octanoic acid (3 mol) are placed in a 1 liter glass reactor equipped with a jacket fed by a thermostatic bath with circulation of oil, a stirring paddle, a thermometer, and a distillation head combined with a condenser and a distillation receiver.

The stirring system is switched on at 400 rpm, and the thermostatic bath is switched on at a nominal temperature of 100° C. When the temperature of the reaction medium reaches 60° C., 2.92 g of p-toluenesulfonic acid (PTSA) monohydrate (2% commercial relative to the dry isosorbide) and 0.90 g of 50% hypophosphorous acid, i.e. 0.3% of dry matter relative to the dry isosorbide, are added. The nominal temperature of the thermostatic bath is then set at 150° C. and the stirring is set at 650 rpm. The mounting assembly is then connected to a vacuum pump equipped with a vacuum gauge, whose nominal pressure is set at 100 mbar.

When the temperature of the reaction medium reaches about 115° C., the water derived from the esterification reaction is distilled off and collected in the receiver. After reaction for 2 hours, the amount of water distilled off corresponds to about 85% of the theoretical amount of water for total reaction. The vacuum is then gradually lowered over a further 3 hours to 25 mbar, while the temperature of the reaction medium naturally reaches 140° C. After reaction for 5 hours, the water distilled off reaches 97% of the theoretical amount.

The reaction medium is then cooled to about 100° C., and the PTSA and hypophosphorous acid strong acids are neutralized by adding 1.8 g of 50% sodium hydroxide. The unreacted octanoic acid is then distilled off under vacuum (5 mbar; vapor temperature: 115° C.). The boiler temperature changes from 130 to 220° C. approximately during this evaporation. After cooling to 100° C., the product is decolorized by treatment with active charcoal. The composition thus purified, known as DEI 1, has a mass amount of isosorbide diester of 99.5%. This composition has a liquid appearance.

Example 2 (According to the Invention)

A Test 2 is performed according to the operating protocol of Test 1, replacing the n-octanoic acid with a mixture of fatty acids consisting of 70% by weight of n-octanoic acid and 30% by weight of n-decanoic acid.

The final composition obtained, known as DEI 2, has a mass amount of isosorbide diesters of 99.4%. This composition has a liquid appearance.

Example 3 (According to the Invention)

A Test 3 is performed according to the operating protocol of Test 1, replacing the n-octanoic acid with a mixture of fatty acids consisting of 60% by weight of n-octanoic acid and 40% by weight of n-decanoic acid.

The final composition obtained, known as DEI 3, has a mass amount of isosorbide diesters of 99.8%. This composition has a liquid appearance.

Example 4 (According to the Invention)

A Test 4 is performed according to the operating protocol of Test 1, replacing the n-octanoic acid with a mixture of fatty acids consisting of 30% by weight of n-octanoic acid and 70% by weight of n-decanoic acid.

The final composition obtained, known as DEI 4, has a mass amount of isosorbide diesters of 99.4%. This composition has a liquid appearance.

Example 5 (Comparative)

A Test 5 is performed according to the operating protocol of Test 1, replacing the n-octanoic acid with n-decanoic acid.

The final composition obtained, known as DEI 5, has a mass amount of isosorbide diester of 99.5%. This composition has a solid appearance.

The volatility of the plasticizing compositions is determined for each of the liquid compositions.

The determination of the volatility of the plasticizing compositions is performed by weight difference after a defined residence time in a ventilated oven. A crystallizing dish is accurately weighed, and an accurately weighed amount of about 5 g of the test product is added thereto. The crystallizing dish is then placed inside the oven at 180° C. for 30 minutes. Once this time has elapsed, the crystallizing dish is placed in a desiccator until cool, and then weighed again. The volatility is then calculated according to the following formula: (starting mass of plasticizer−mass of plasticizer after residence in the oven)×100/starting mass of plasticizer.

The distribution of the isosorbide diesters (A), (B) and (C) in the compositions of Tests 1 to 5 is featured in Table 1 below, along with the volatility for compositions DEI 1 to DEI 4.

TABLE 1

|  | DEI 1 | DEI 2 | DEI 3 | DEI 4 | DEI 5 |
| --- | --- | --- | --- | --- | --- |
| Diester (A) | 100% | 48% | 38% | 10% | 0% |
| Diester (B) | 0% | 43% | 47% | 43% | 0% |
| Diester (C) | 0% | 9% | 15% | 47% | 100% |
| Volatility (%) | 0.95 | 0.77 | 0.47 | 0.44 |  |

Only compositions DEI 1 to 4 have a liquid appearance at room temperature.

Composition DEI 5 is solid, which poses handling problems (impossible to pump or to pour), for example when it is desired to use it for plasticizing polymers.

Compositions DEI 1 to 4 will now be used for plasticizing polymer in Examples 6 and 7 below.

Example 6 (Evaluation of the Mechanical Properties)

Formulations of PVC plasticized according to the invention are prepared using the following products:
PVC Marvylan® S7102: 100 parts
Stabilizer Baerostab® NT 319P (Ca/Zn powder): 1.5 parts
Co-stabilizer Baerostab® LSA (epoxidized soybean oil): 2 parts
Plasticizer: 34 parts The preparation of pressed specimens for characterizing the mechanical properties is performed in several steps.

In a first stage, it is necessary to plasticize PVC powder with the plasticizing composition in a Planetmix 500 planetary mixer (from the company Thermo Scientific) equipped with a temperature regulation circuit. A mass of 500 g of PVC is introduced into the mixer, with the corresponding amount of thermal stabilizer and of thermal co-stabilizer. When the temperature of the mixture reaches 85° C., the plasticizing composition is incorporated over the entire surface of the PVC powder. The preparation is then mixed for a further 8 minutes after absorption of the plasticizer into the PVC.

In a second stage, plates of plasticized PVC are formed using a Carver press and a mirror-polished stainless-steel 30×30 cm mold equipped with a frame 2 mm thick and a mirror-polished stainless-steel lid. An amount of 180 g of plasticized PVC powder is uniformly poured into the frame placed inside the mold, and the whole is then covered with a lid. The assembly is placed on the plateau of the press preheated to 185° C. and the program which consists in applying a closing force of 18 000 kg at 185° C. for 2 minutes is started. After cooling to a temperature close to 45° C., the PVC plate thus obtained is then removed from the mold.

The final step consists in cutting out 10 specimens of 5A type (dimensions: 25 mm×4 mm; 2 mm thick) with the aid of a punch using the plasticized PVC plates obtained as described previously.

These specimens are then characterized in traction on a tensile testing bed or extensometer of Instron type, model 5966, with the following parameters: throughput speed=50 mm/min; cell=5 KN. The prestressing is rezeroed once the specimen is in place and the jaws have been tightened. The extensometer plots the stress/strain curve of the specimen up to the point of failure. At the end of the test, the stress values at 100% strain and the ultimate strain values are recorded.

Table 2 below shows, for each composition tested, the stress values at 100% strain and ultimate strain values obtained.

TABLE 2

| Plasticizer | Stress at 100% strain (MPa) | Ultimate strain or elongation (%) |
| --- | --- | --- |
| DEI 1 | 16.6 | 295 |
| DEI 2 | 16.9 | 326 |
| DEI 3 | 17.3 | 308 |
| DEI 4 | 17.5 | 337 |

These tests show that the compositions according to the invention plasticize the polymer at least as satisfactorily as the DEI of the prior art.

Example 7 (Effect on the Migration Properties of the Plasticizing Composition)

One of the essential criteria for any plasticized polymer is the degree of migration of the plasticizing composition used.

Specifically, it should be minimal if it is desired to preserve the properties of the material over time.

Preparation of the Tests:

Starting with a plasticized PVC plate as prepared in Example 1, PVC specimens are cut out (40×40 mm, 2 mm thick). They are conditioned for 72 hours at 20° C.—65% RH. For each PVC specimen to be tested, two absorbent supports of non-plasticized PVC of Komadur type (from the company Sigma PLV) of dimensions 80×80 mm by 1 mm thick are prepared. The specimens and the absorbent supports are weighed on a precision balance. The plasticized PVC specimens are then placed between the two absorbent supports, at their center. This assembly is placed between two glass plates, and a 5 kg weight is then placed on top. The whole is placed in a ventilated oven at 70° C. for one week. After one week in the oven, the specimens are reconditioned at 20° C.—65% RH for 2 days. Finally, they are weighed again in order to determine the degree of migration of the specimen via the following calculation:

(mass of specimen before baking−mass of specimen after baking)×100/mass of specimen before baking.

The reduction in the degree of migration relative to DEI 1 of the prior art is also calculated.

The results are presented in Table 3 below.

TABLE 3

| Plasticizer | Degree of migration (%) | Reduction in the degree of migration relative to DEI 1 |
| --- | --- | --- |
| DEI 1 | 1.61 | |
| DEI 2 | 1.31 | −19% |
| DEI 3 | 1.22 | −24% |
| DEI 4 | 1.08 | −33% |

This table shows that the compositions according to the invention make it possible to reduce the degree of migration relative to DEI 1 of the prior art.

This reduction is particularly pronounced for DEI 4.

The invention claimed is:

1. A composition comprising: at least 80% up to about 99% by mass of diesters relative to a total mass of the composition, wherein said composition comprises:

from 5% to 57% by mass of diester (A) of formula:

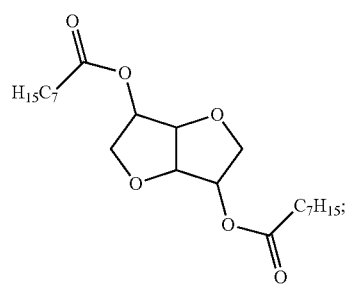

from 37% to 55% by mass of diester (B) of formula:

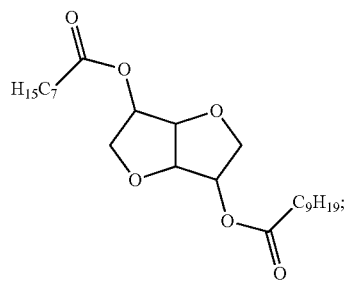

and from 5% to 57% by mass of diester (C) of formula:

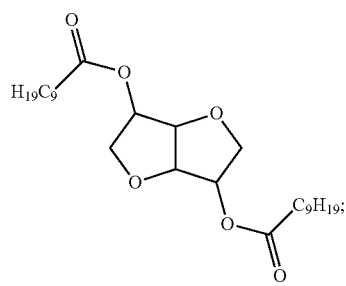

the amounts of diester (A), diester (B), and diester (C) being expressed relative to a total mass of diesters (A), (B), and (C), and wherein said composition is suitable for plasticizing a polymer.

2. The composition as claimed in claim 1, comprising: from 5% to 57% by mass of diester (A); from 37% to 54% by mass of diester (B); and from 5% to 57% by mass of diester (C).

3. The composition as claimed in claim 1, comprising: from 5% to 43% by mass of diester (A); from 37% to 53% by mass of diester (B); and from 11% to 57% by mass of diester (C).

4. The composition as claimed in claim 1, comprising: from 5% to 31% by mass of diester (A); from 37% to 52% by mass of diester (B); and from 19% to 57% by mass of diester (C).

5. The composition as claimed in claim 1, wherein: diester (A) has the following formula:

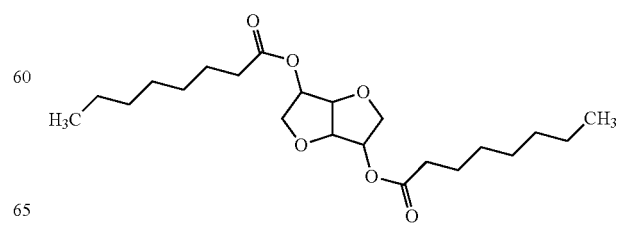

diester (B) has the following formula:

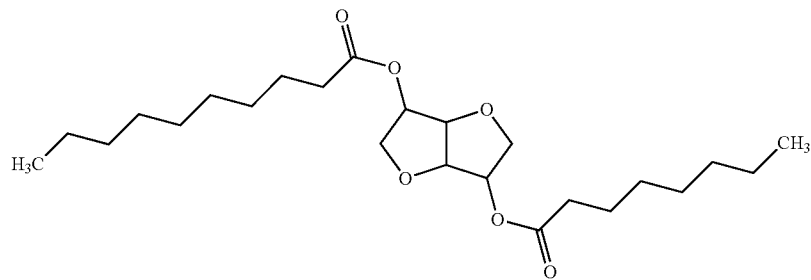 [SMILES: CCCCCCCCCC(=O)OC1COC2C(OC(=O)CCCCCCC)COC12]

and
diester (C) has the following formula:

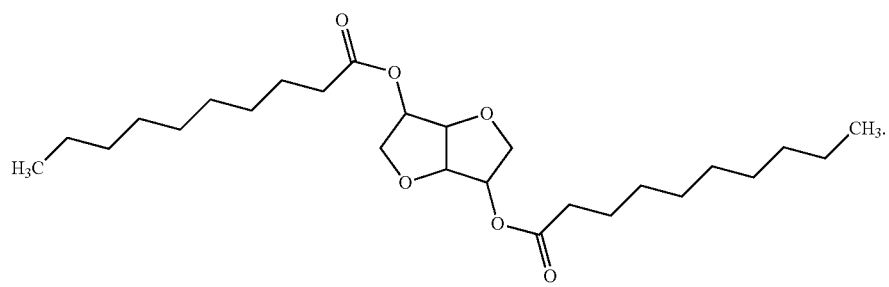 [SMILES: CCCCCCCCCC(=O)OC1COC2C(OC(=O)CCCCCCCCC)COC12]

6. The composition as claimed in claim 1, wherein said polymer is selected from the group consisting of vinyl polymers, polyurethanes, polyesters, cellulose-based polymers, starches, acrylic polymers, polyacetates, natural or synthetic rubbers, polyamides, and mixtures of these polymers.

7. The composition as claimed in claim 1, wherein said polymer is polyvinyl chloride.

* * * * *